(12) United States Patent
Atassi et al.

(10) Patent No.: US 7,541,159 B2
(45) Date of Patent: Jun. 2, 2009

(54) MOLECULAR-SPECIFIC UROKINASE ANTIBODIES

(75) Inventors: M. Zouhair Atassi, Houston, TX (US); Dennis R. Morrison, Kemah, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 501 days.

(21) Appl. No.: 10/828,531

(22) Filed: Apr. 14, 2004

(65) Prior Publication Data

US 2005/0233397 A1    Oct. 20, 2005

(51) Int. Cl.
*G01N 33/573* (2006.01)
*G01N 33/577* (2006.01)

(52) U.S. Cl. .................... 435/7.4; 436/548; 530/388.26
(58) Field of Classification Search .................. 435/7.4; 436/548; 530/388.26
See application file for complete search history.

(56) References Cited

U.S. PATENT DOCUMENTS

| | | | |
|---|---|---|---|
| 4,474,756 | A | 10/1984 | Mitsuhashi et al. |
| 4,600,580 | A | 7/1986 | Smith |
| 4,673,573 | A | 6/1987 | Ferres et al. |
| 4,741,903 | A | 5/1988 | Smith |
| 4,791,068 | A | 12/1988 | Loskutoff et al. |
| 4,873,083 | A | 10/1989 | Hunter et al. |
| 5,869,238 | A * | 2/1999 | Morrison ........................ 435/6 |
| 2005/0232924 | A1* | 10/2005 | Mazar et al. .............. 424/146.1 |

OTHER PUBLICATIONS

Lederman et al, Molec. Immunol., 28, 1171-1181, 1991.*
Morrison et al; Electrophoretic Separation of Kidney and Pituitary Cells on STS-8; Adv. Space Res.; vol. 4, No. 5, pp. 67-76, 1984, Great Britain.
Sibley et al; Enhancement Effect of Storage Buffer on Regeneration of Immunosorbent Surfaces; Benchmarks.
Verstraete et al; Pharmacology of Thrombolytic Drugs; JACC vol. 8, No. 6, Dec. 1986, pp. 33B-40B, Leuven, Belgium.
Barlow et al; Secretion of plasminogen actiator by the human macrophage-like cell line, GCT . . . ; British Journal of Haematology, 1982, 52, pp. 645-655.
Swank et al; Parallel line analysis: multifunctional software for the biomedical sciences; Computer Methods and Programs in Biomedicine, 33 (1990) pp. 95-105.
Barlow et al; Identification of the Plasminogen Activator(s) producted by the Transformed Liver Cell Line, SK-HEP-1; Thrombosis Research 32; 1983, pp. 29-34.
Schmitt et al; Tumour-associated fibrinolysis: the prognostic relevance of plaminogen activators uPA and tPA in . . . ; Blood Coagulation and Fibronolysis, 1990, pp. 695-702.
Hasui et al; Comparative Study of Plasminogen Activators in Cancers and Normal Mucosae of Human Unirary Bladder; Cancer Research 49, 1067-1070, Feb. 15, 1989.
Gaylis et al;Plasminogen Activators in Human Prostate Cancer Cell Lines and Tumors: Correlation with the Aggressive Phenotype; The Journal of Urology; vol. 142, 1989, pp. 193-198.
Verstraete et al; Thrombolytic Therapy in the Eighties; Journal of the American Society of Hematology; vol. 67, No. 6Jun. 1986, pp. 1539-1541.
Schmitz et al; Production of Monoclonal Antibodies with Pre-Selected Submolecular Binding Specificities to Protein . . . ; Molecular Immunology; vol. 19, No. 12, pp. 1699-1701.
Acton et al; Eukaryotic Cell Cultures Basics and Applications; Plenum Press; pp. 241-267.
Erickson; Metastatic Machinatiuns; Scientific American, Jul. 1992, pp. 110-111.
Morrison et al; Experiment Sequence Test Report for Biorack Experiment 01.2-I, "Antigen"; International Microgravity Laboratory Mission No. 2 (IML-2).
Morrison et al; Preliminary Science Report No. 2; IML-2 STS-65; Apr. 21, 1995.
Atassi; Analysis of Electrophoresis Samples and Antibody Applications; Final Progress Report NAS9-18065; Oct. 24, 1995.
Atassi; Analysis of uPA in Supernatants from Kidney Cell Culture Flight Samples; Contract No. NAS9-18065.

* cited by examiner

*Primary Examiner*—David Saunders
(74) *Attorney, Agent, or Firm*—Theodore U. Ro

(57) ABSTRACT

Antibodies have been developed against the different molecular forms of urokinase using synthetic peptides as immunogens. The peptides were synthesized specifically to represent those regions of the urokinase molecules which are exposed in the three-dimensional configuration of the molecule and are uniquely homologous to urokinase. Antibodies are directed against the lysine 158-isoleucine 159 peptide bond which is cleaved during activation from the single-chain (ScuPA) form to the bioactive double chain (54 KDa and 33 KDa) forms of urokinase and against the lysine 135 lysine 136 bond that is cleaved in the process of removing the alpha-chain from the 54 KDa form to produce the 33 KDa form of urokinase. These antibodies enable the direct measurement of the different molecular forms of urokinase from small samples of conditioned medium harvested from cell cultures.

12 Claims, 2 Drawing Sheets

COMPARISON OF THREE TYPES OF UROKINASE ASSAYS

MOLECULAR-SPECIFIC UROKINASE ANTIBODIES

ORIGIN OF THE INVENTION

The invention described herein was made at least in part in the performance of work under a NASA contract and is subject to Public Law 96-517 (35 U.S.C. §200 et seq.). The contractor has not elected to retain title to the invention.

FIELD OF THE INVENTION

The invention relates to compositions and methods of using antibodies to analyze molecular forms of urokinase. More particularly, a group of such antibodies, each of which recognizes and selectively binds to one of several molecular forms of urokinase, is used to detect, quantitate or purify individual forms of urokinase. Species of urokinase that can be analyzed using the compositions and methods of the invention include the inactive 54,000 dalton single chain form, the bioactive, 34,000 dalton double-chain form and the bioactive 33,000 dalton form.

DESCRIPTION OF THE RELATED ART

Urokinase is one member of a class of proteins known as fibrinolytic proteins. Other fibrinolytic proteins include streptokinase and tissue plasminogen activator (tPA). These type proteins aid in natural blood clot dissolution. Blood clot dissolution is an important therapy in the treatment of several major debilitating and life threatening diseases including myocardial infarction associated with heart attacks, stroke, deep vein thrombosis and pulmonary embolus.

Urokinase is more specifically a serine protease. Its natural substrate is plasminogen, which it converts to bioactive plasmin. When plasmin comes in contact with the major structural component of blood clots called fibrin, the fibrin is degraded into small fragments dissolving the clot.

Consequently, there is great interest in urokinase as a therapeutic agent. U.S. Pat. No. 4,873,083 discloses a fibrinolytic composition employing an enzyme such as urokinase tissue plasminogen activator and a surface active copolymer for the treatment of thrombosis. U.S. Pat. Nos. 4,600,580, 4,673, 573, and 4,741,903 disclose chemically-modified forms of urokinase that employ urokinase for fibrinolytic activity in therapeutic applications. U.S. Pat. No. 4,791,068 discloses the use of a polyclonal antibody system for detecting an inhibitor of urokinase-type plasminogen activator and its use in diagnostic assays.

For these reasons, there is also great interest in developing more efficient methods of urokinase production. U.S. Pat. No. 4,889,808 discloses a method of enhancing the production of a single chain urokinase by the addition of heparin and a cell growth factor to culture medium of cells producing the enzyme. The production levels were determined using polyclonal goat antisera which was not specific for active forms of urokinase, but did allow crude detection of enhanced levels of production.

Another approach is to isolate novel cell lines that produce large quantities of this protein. Urokinase is known to be secreted by kidney cells, some neoplastic tissues, as well as embryonic cell line (Bernick and Kwann, *J. Clin. Invest.* 48:1740-1753 (1969); Barlow et al., *Thrombosis Res.*, 32:29-34 (1983)). Bernick and Kwann (*J. Lab. Clin. Med.* 70:650 (1967)) have reported that only 5-10% of the cells from human embryonic kidney (HEK) produce plasminogen activators. Enhanced production can be achieved if cells producing urokinase are isolated from those cells that do not produce urokinase. When a heterogeneous sample of renal cells is separated under microgravity conditions by continuous flow electrophoresis, several distinct subgroups can be isolated. To determine which subgroup most efficiently produces urokinase, sensitive and specific assay methods that can detect the various molecular forms and total urokinase are required.

Since urokinase is a cancer-specific protein, it is a marker of neoplastic cell development, particularly in cases of invasion and metastasis where this enzyme can play an important role. The role of urokinase in cancer has been discussed as it relates to breast cancer (Schmitt et al., *Blood Coagulation and Fibrin.* 1:695 (1990), urinary cancer (Hasui et al., *Cancer Res.* 49:1067 (1989), and prostate cancer (Gaylis et al. *J. Urology* 142:193 (1989)). Thus, sensitive and specific assays are also needed which can be used to diagnose these conditions.

Urokinase is synthesized as a single polypeptide of 431 amino acid residues. An amino terminal signal peptide of 20 amino acids (−20 to −1) is cleaved from the polypeptide as it is processed during export from the cell, leaving a 411 amino acid protein (1-411) that is called the urokinase zymogen or single chain urokinase plasminogen activator (scuPA).

Urokinase zymogen has very little or no enzymatic activity. Activation of the urokinase zymogen involves cleavage of the peptide bond between lysine 158 and isoleucine 159 and the loss of lysine 158 to form the high molecular weight (HMW) 54,000 dalton active enzyme (Verstraete and Collen, *Blood* 67:1529-1541 (1986). Activation can also include (in addition to 158-159 cleavage) cleavage of the bond between lysine 135 and lysine 136 followed by loss of the amino terminal 135 amino acids (the "A chain") leaving an active low molecular weight (33,000 dalton) enzyme. The non-enzymatic products of these cleavage events are rapidly degraded. Activation and autodegradation of urokinase in a cell culture can result in all three types of urokinase being present in culture medium at one time.

To identify cell populations that express increased levels of urokinase a quantitative measurements of all forms of urokinase is necessary. To be of practical use, such assays must be sensitive enough that urokinase production from small numbers of cells can be analyzed. Such assays must also be relatively easy to perform so that large numbers of samples containing as many as $5\text{-}10 \times 10^4$ cells/ml or more can be tested.

Current urokinase assay methods are cumbersome. One of the common procedures is the fibrin plate lysis assay. See, e.g., U.S. Pat. No. 4,741,903; and, Lewis et al., "Problems in the Bioassay of Products from Cultured HEK Cells: Plasminogen Activator" in *Eukaryotic Cell Cultures: Basics and Applications* 172 Plenum Press, New York 1984. This assay measures fibrinolytic activity. Test samples are incubated with fibrin clots and the increase in the diameter of the clot lysis zone is measured as a function of time. The rate of clot disappearance is a measure of fibrinolytic activity. The detection limit for such assays is generally 10-15 I.U./ml. Other assays include the timed clot-lysis assay (Swank et al. *Computer Meth. Programs Biomed.*, 33:95-105 (1990)), $^{125}$I-labeled fibrinogen assay and colorimetric assays which use synthetic chemical substrates, and the S-2444 assay, KabiVitrum, Sweden (Claeson et al., *Haemostasis* 7:76-78 (1978). Assays such as these are also activity assays since they are based on measurement of fibrinolytic activity. They are used to detect and quantitate active urokinase but are incapable of detecting the inactive zymogen.

Furthermore, existing assays are inadequate to detect small quantities of uPA in very small (e.g. 10 µl) samples of culture medium or bodily fluids. Thus, such assays may not identify potentially important cell lines that produce large quantities of the urokinase zymogen (scuPA). The scuPA levels can be approximated by preincubation of samples with plasmin (which activates urokinase zymogen) followed by an activity assay. However, additional steps in an already cumbersome assay increase the variation in assay results. Moreover, it is difficult to determine the amount of plasmin and hydrolysis times needed to fully activate zymogen in all cases.

Inconsistent test results are frequently associated with fibrin clot activity assays. For example, storage of samples affects apparent activity, dose response curves are nonlinear, and replicate cell cultures produce variable activities. More importantly, protein diffusion is a factor affecting the apparent activity of urokinase. The 33,000 dalton form diffuses faster than the 54,000 dalton form increasing the apparent activity relative to the 54,000 dalton form. Although the chromogenic assay is not limited by protein diffusion, this assay is not as sensitive as the fibrin clot assay. Sample composition can greatly affect activity measurements, for example the presence of inhibitors of urokinase may greatly reduce the amount of activity measured for a given amount of enzyme. Similarly, other non-urokinase fibrinolytic enzymes in the sample may interfere by increasing the apparent activity. Moreover, these assays are not sensitive enough to detect urokinase produced from different subpopulations of small numbers of cells.

Activity assays also are unable to distinguish between various active forms of urokinase since they only measure total fibrinolytic activity. This makes comparisons between samples difficult. Use of a combination of assays, such as the clot lysis assay in combination with the chromogenic assay, can give approximate estimates of the ratios of the 54,000 and the 33,000 dalton forms of urokinase. However, this is a cumbersome and time-consuming procedure.

An alternative approach to analysis of the urokinase from cell culture is to use quantitative immunological techniques such as enzyme linked immunosorbent assays (ELISA) or radioimmunoassays (RIA). Various murine and rabbit IgG monoclonal antibodies are available against the A-chain (residues 1-135) or B-chain (residues 159-411) of urokinase (i.e., American Diagnostica, New York). These antibodies are made from animals immunized with the major molecular forms of urokinase. U.S. Pat. No. 4,474,756 discloses a method of producing antibodies by immunization of animals with a whole protein, such as human urokinase, after chemically crosslinking the protein to a polysaccharide. However, since urokinase has more than 70% homology with trypsin and significant homology to other serine proteases and tissue plasminogen activator (tPA), specificity is a problem. Therefore, non-specific antibodies such as these also bind to and detect other serine proteases and fibrinolytic proteins, and they do not give reliable quantitative estimates of urokinase in samples.

Thus, compositions and methods are needed that can sensitively and specifically quantitate urokinase in all its forms in a sample. Assays are needed which overcome the cumbersome aspects of existing methods and which produce less variable results and which are not subject to interferences from inhibitors which could contaminate sample preparations. Assays are needed which are specific for urokinase and which distinguish between closely related proteins such as tissue plasminogen activator or streptokinase or homologous serine proteases that increase the "apparent" concentration of urokinase observed in samples making existing assays inaccurate. Lastly, assays are needed which are capable of measuring the concentration of each form of urokinase in a sample.

SUMMARY OF THE INVENTION

In accordance with the present invention, polyclonal and monoclonal antibody compositions are provided that can sensitively and specifically quantitate urokinase in all its forms. The compositions provided can be used in methods that are convenient to perform, give reliable results, and are free from interferences from enzyme inhibitors that could affect fibrinolytic activity measurements. The compositions are specific for urokinase and will not detect closely related proteins such as tissue plasminogen activator or homologous serine proteases. Compositions provided with this invention can be used to measure the concentration of each form of urokinase even in a small sample.

Antibodies (polyclonal and monoclonal) were generated against urokinase by employing synthetic peptides as immunogens. The antibodies that are generated by injecting an immunogen into an animal are said to be "directed against" that immunogen. Antibodies directed against immunogens may bind to other molecules as well. Particularly, antibodies directed against an immunogen may bind to other biological macromolecules that contain the immunogen. In particular, where as here the immunogen is a peptide which represents a particular portion of the urokinase macromolecule, antibodies directed against the peptide immunogen can bind to the biological macromolecule urokinase in any of its forms which contains the immunogen peptide sequence. If the immunogen is found on one macromolecule or a subset of macromolecules, and the antibody directed against that immunogen binds preferentially to that macromolecule or subset of macromolecules, the antibody is said to have "specific" binding for that macromolecule or subset of macromolecules. "Specific" binding is merely a reflection of the fact that the binding affinity of the antibody to macromolecules containing the immunogen is higher than the binding affinity of the same antibody to other molecules.

In certain aspects, the invention relates to an antibody directed against a peptide whose sequence is chiefly derived from the urokinase amino acid sequence (Seq. ID No. 16). "Chiefly derived" for purposes of this invention means that the sequence of the peptide is virtually identical to at least a portion of a linear sequence of urokinase except for minor alteration such as additional terminal residues or substitutions of cysteine residues to prevent internal disulfide linkages (i.e., see Seq. ID No. 5 where cysteine-131 is replaced by a glycine residue in the peptide to prevent disulfide formation with cysteine-126).

The antibody is first characterized by its capability to specifically bind to urokinase. As further amplified in the claims, the characteristic of specific binding to urokinase is such that the antibody possesses a substantially lower binding affinity to proteins other than urokinase than that it has for urokinase. Importantly, this reduced binding affinity for non-urokinase proteins includes those proteins as similar in amino acid sequence to that of urokinase as is trypsin, a protein with a high degree of sequence homology with urokinase.

One group of antibodies that meet this general description will be antibodies which bind to the amino terminal end of urokinase. The amino terminal end of the urokinase molecule for purposes of the invention comprise urokinase amino acid residues 1-135 of Seq. ID No. 16.

Among those antibodies which are specific for the amino terminal end of the urokinase molecule will be those antibodies directed against one or more of six specific peptides. These peptides may be any one of a number of such peptides based upon sequences of the amino terminal sequence of urokinase such as: SNELHQVPSNCD (Seq. ID No. 1), RGKASTDT-MGRPCLP (Seq. ID No. 2), CRNPDNRRRP (Seq. ID No. 3), RNPDNRRRPWC (Seq. ID No. 4), CMVHDGADGK (Seq. ID No. 5) or MVHDCADGK (Seq. ID No. 6). In certain instances, an original residue found in urokinase will be altered for ease of synthesis which alteration does not materially affect the immunological response to the synthetic peptide (e.g., instead of asparagine-10 as in urokinase, Seq. ID No. 1 possesses an aspartate; instead of cysteine-131, Seq. ID No. 5 possesses a glycine).

Another group of antibodies that meet this general description will be antibodies which bind to the carboxyl terminal end of urokinase. The carboxyl terminal end of the urokinase molecule for purposes of the invention comprise urokinase amino acid residues 159-411 of Seq. ID No. 16.

Among those antibodies which are specific for the carboxy terminal end of the urokinase molecule will be those antibodies directed against one or more of six specific peptides. These peptides may be any one of a number of such peptides based upon sequences of the amino terminal sequence of urokinase such as: YRRHRGGSVTYVC (Seq. ID No. 7), CFIDYP-KKEDY (Seq. ID No. 8), SRLNSNTQGEMK (Seq. ID No. 9), SMYNDPQFGTSC (Seq. ID No. 10), LISHRECQQ-PHYYGSEVTTKMLC (Seq. ID No. 11), or SHT-KEENGLAL (Seq. ID No. 12).

Other antibodies which meet the general descriptions provided by the antibodies of the invention include antibodies which can detect cleavage sites in urokinase. These antibodies include an antibody which has a binding site that includes the peptide bond between lysine 158 and isoleucine 159. More specifically, such an antibody will be one which is directed against one or more of two peptides selected from the group of peptides comprising PRFKIIG (Seq. ID No. 13) or RPRFKIIGGE (Seq. ID No. 14). These antibodies also include an antibody which has a binding site that includes the peptide bond between lysine 135 and lysine 136. More specifically, such an antibody will be one which has a lower binding affinity for urokinase when no chemical bond exists between lysine 158 and isoleucine 159. Similarly, such an antibody will be one which has a lower binding affinity for urokinase when no chemical bond exists between lysine 135 and lysine 136. The site defined by lysine 135 and lysine 136 is the natural cleavage site of the urokinase proenzyme and is structurally exposed to cleavage, and thus is a likely natural epitope region. This site is bridged by Seq. ID No. 17.

Particularly, in a preferred embodiment, an antibody directed against the peptide sequence RPRFKIIGGE (Seq. ID No. 14), with a binding affinity constant for the urokinase zymogen of at least $1 \times 10^8$ M$^{-1}$, is disclosed which additionally exhibits the binding affinity constant for urokinase lacking a peptide bond between lysine 158 and isoleucine 159 decreased by at least ten-fold.

It is also possible to make multimers of peptides by covalently linking one or more of peptides in Seq. ID Nos. 1-15. Thus, duplex peptides may easily be covalently linked by disulfide linkages, as for example by making (102-111)-(126-135), (59-73)-(103-113), (177-189)-(205-215). It is also possible to cause a peptide to form an internal disulfide, as for example in 319-341 (Seq. ID No. 11).

It will be recognized by one of skill in the art of making antibodies against specific peptides, that such antibodies may be derived from polyclonal sera. Alternatively, and in certain aspects, preferably, the antibody of any of the embodiments mentioned above may be a monoclonal antibody. More specifically, the monoclonal antibodies of the invention have been given the designations: A3-E5-A7, A3-E5-B8, A3-E5-G10, A3-E5-H12, A3-E5-B3, C2-A4-H4, C2-A4-F10, C2-A4-F11, D4-A5-E7, D4-C1-A5, D4-C1-G4, D4-C6-A4, D4-C6-A8, D4-C6-E12, D4-C6-F7 or D4-C6-G12. Hybridoma cell lines capable of producing such monoclonal antibodies are also provided. While these specific monoclonal antibodies and the hybridomas that produce them represent the results of the particular experiments defined in greater detail below, they are in merely exemplary in nature. Using the sequences selected and disclosed in the invention, the normally skilled practitioner may readily obtain antibodies with the same characteristics as reported here and which will function identically to those reported here by first obtaining one or more peptides that "correspond to" one or more predetermined sequences of amino acids. The following three paragraphs describe the meaning of the term "corresponding to" and its derivatives in greater detail.

The peptides will be one of the group of peptides disclosed in Sequence ID Nos. 1-15. It will be recognized, however, by those of skill in the art that the catalysts described above and those claimed in general may contain functionally equivalent amino acid substitutions. The importance of the hydropathic index of amino acids in conferring biological function on a peptide is generally known by those of skill in the art. It has been found by many researchers that certain amino acids may be substituted for other amino acids having a similar hydropathic index or score and still retain similar if not identical biological activity. As displayed below, amino acids are assigned a hydropathic index on the basis of their hydrophobicity and charge characteristics. It is believed that the relative hydropathic character of the amino acid determines the secondary structure of the resultant peptide, which in turn defines the interaction of the peptide with the substrate molecule. It is proposed that biological functional equivalence may typically be maintained where amino acids are exchanged having no more than a ±1 to 2 difference in the index value, and more preferably within a ±1 difference.

| AMINO ACID | HYDROPATHIC INDEX |
|---|---|
| Isoleucine | 4.5 |
| Valine | 4.2 |
| Leucine | 3.8 |
| Phenylalanine | 2.8 |
| Cysteine/Cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and might still obtain a peptide having similar biological activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, although these are not the only such substitutions, the preferred substitutions which take various of the foregoing characteristics into consideration include the following:

| ORIGINAL RESIDUE | EXEMPLARY SUBSTITUTIONS |
|---|---|
| alanine | glycine; serine |
| arginine | lysine |
| asparagine | glutamine; histidine |
| aspartic acid | glutamic acid |
| cysteine | serine |
| glutamine | asparagine |
| glycine | alanine |
| histidine | asparagine; glutamine |
| isoleucine | leucine; valine |
| leucine | isoleucine; valine |
| lysine | arginine; glutamine; glutamic acid |
| methionine | leucine; tyrosine |
| serine | threonine |
| threonine | serine |
| tryptophan | tyrosine |
| tyrosine | tryptophan; phenylalanine |
| valine | isoleucine; leucine |

In addition to the compositions provided by the invention, methods are disclosed which utilize the anti-urokinase antibody compositions in a variety of ways. Thus, in one embodiment, a method of detecting urokinase zymogen in a sample is provided. This method comprises standard plate assays including solid phase plate radioimmunoassay or enzyme linked immunoassays (ELISA). Another method made possible by the anti-urokinase antibody compositions of the invention include detecting urokinase associated with the surface of a cancer cell. This method comprises using the antibodies of the invention to detect urokinase levels in a cell population, which levels are correlated to DNA content for evaluation of potential of tumor cells.

For whatever purpose the quantitation is accomplished, the technique will be similar in its use of the peptides of the invention. Thus, Seq. ID Nos. 1-15 can be used to generate immunological compositions capable of recognizing the urokinase zymogen. The same is true of a peptide comprising residues 135 and 136 of Seq. ID No. 16. When the same battery of immunological compositions is used against the high molecular form of urokinase which lacks the 158-159 peptide bond, each such composition will bind the high molecular weight form of urokinase except immunological composition derived from Seq. ID Nos. 13 and 14, thusly providing a test to distinguish the inactive zymogen from the active high molecular weight form of urokinase. The same battery of immunological compositions is useful in distinguishing the low molecular weight form will not efficiently bind immunological compositions derived from Seq. ID Nos. 1-6, 13-14 or from a peptide comprising residues 135 and 136 of Seq. ID No. 16.

Diagnostic kits for detecting the presence and quantity of urokinase in a sample are also provided. Such kits comprise effective amounts of the antibodies which individually bind to the amino terminal end of urokinase, the carboxyl terminal end of urokinase, the binding site that includes the peptide bond between lysine 158 and isoleucine 159, and the binding site that includes the peptide bond between lysine 135 and lysine 136. Additionally, each such antibody includes an indicating group capable of detecting binding of the antibody to a target molecule and standards of an effective concentration of each of the bioactive and inactive forms of urokinase detectable using the four antibodies included in the kit.

DESCRIPTION OF PREFERRED EMBODIMENTS

Figure 1:
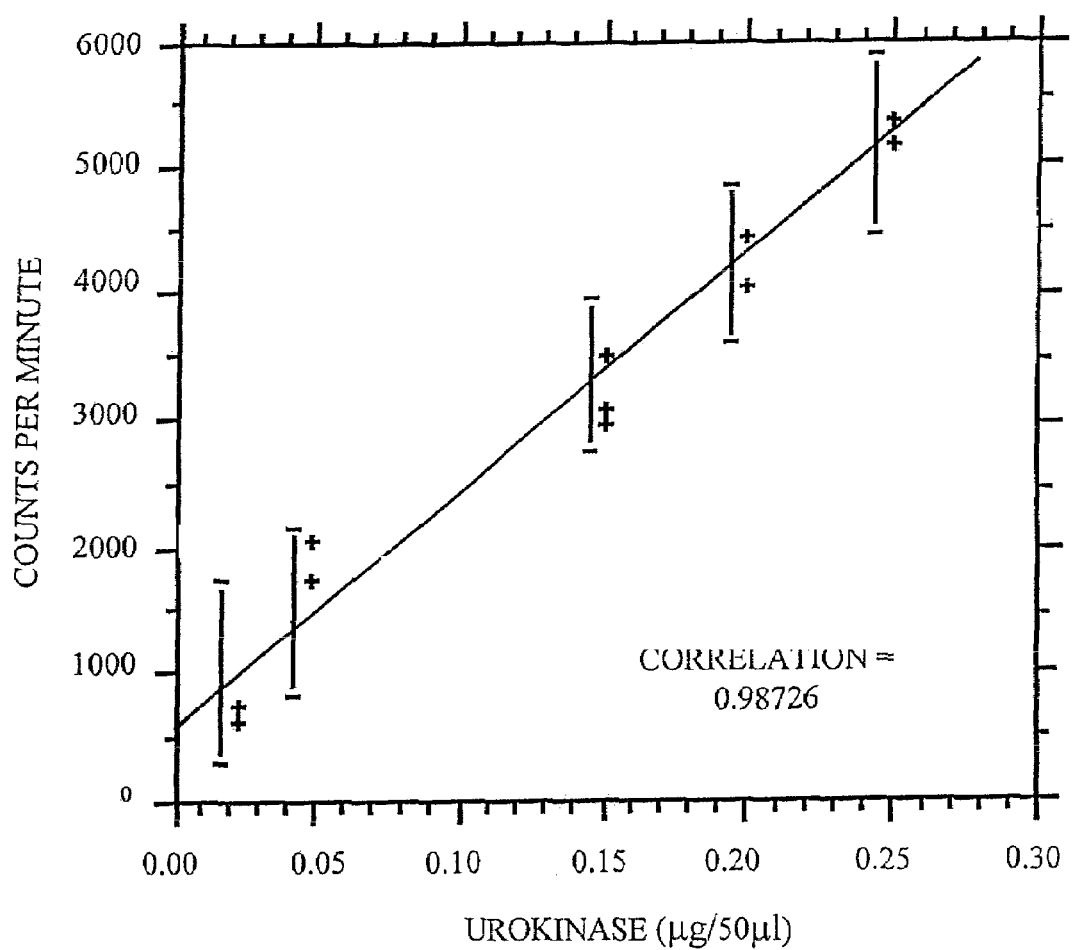
FIG. 1: Standard curve for Run 4 Day 12 supernatants radioimmunoassay.

With respect to the inactive form of urokinase (See Seq. ID No. 16), activation of the zymogen involves cleavage of the peptide bond 158-159 and the loss of Lys-158. An active form of the enzyme is produced which has the sequence 1-157 (A chain) linked to sequence 159-411 (B chain) by a disulfide bond between Cys-148 and Cys-249. Another active form of the enzyme has sequence 136-157 (A1 chain) linked to sequence 159-411 (B chain). The various regions selected for synthesis correspond to sequences 1-12 (Seq. ID No. 1), 59-73 (Seq. ID No. 2), 102-111 (Seq. ID No. 3), 103-113 (Seq. ID No. 4), 126-135 (G at 131) (Seq. ID No. 5), 127-135 (Seq. ID No. 6), 177-189 (Seq. ID No. 7), 205-215 (Seq. ID No. 8), 222-233 (Seq. ID No. 9), 319-330 (Seq. ID No. 10), 319-341 (Seq. ID No. 11), 401-411 (Seq. ID No. 12), 155-161 (Seq. ID No. 13) and 154-163 (Seq. ID No. 14). In addition, the following peptide pairs will be linked by disulfide bonds: (59-73), (102-111)-(126-135, G131) and (177-189)-(205-215). The covalent structures of the peptides that have been (or are being) synthesized are shown in Table 1. The single letter notations of the amino acids are: A, alanine; C, cysteine; D, aspartic acid; E, glutamic acid; F, phenylalanine; G, glycine; H, histidine; I, isoleucine; K, lysine; L, leucine, M, methionine; N, asparagine; P, proline; Q, glutamine; R, arginine; S, serine; T, threonine; V, valine; W, tryptophan; Y, tyrosine.

Peptide Immunogen Synthesis

The peptides used for certain particular examples of the invention correspond to the Sequence ID Nos. 1-6. These peptides, as well as other peptides produced using the methods of the invention, are synthesized either by t-butyloxycarbonyl (t-Boc) on a phenylacetamidomethyl (PAM) resin or by 9-fluorenmethylcarbonyl (Fmoc) amino acids on a benzyloxyvbenxyl alcohol resin as described elsewhere (McCormick and Atassi, *Biochem. J.*, 224:9950-10000 (1984); Mulac-Jericevic and Atassi, *J. Prot. Chem,* 6:365-373 (1987); Atassi et al., *Proc. Natl. Acad. Sci. USA,* 88:3613 (1991), together with methods for purification and characterization of the peptides.

Peptide immunogens can be synthesized chemically by the well known methods discussed above. They can also be isolated by purification after proteolysis of individual forms of urokinase. Particular care must be given to the choice of protease used in the latter method so that desired epitomes are not destroyed.

To avoid generating antibodies that cross react with other known proteins peptide immunogen sequences are selected which are unique to urokinase. To determine which sequences are unique to urokinase, the urokinase sequence can be aligned with other proteins whose sequences are known. Many of these protein sequences can be found in data bases and convenient computer programs can be enlisted to perform a homology search. Such searches may be accomplished using the FAST-DB (Fast Pairwise Comparison of Sequences—Release 5.4) sequence homology searching program as provided by Intelligenetics, Inc., 700 East El Camino Real, Mountain View, Calif. 94040. The searches may be conducted in the publicly-available sequence databases—PIR39 and Swiss-Prot 28.

Fourteen peptides were prepared for use as immunogens. Peptides derived from the amino terminal end of the urokinase protein, including residues 1 through 135, were used to generate antibodies specific for the A chain of urokinase. Six peptides represent areas present only in the zymogen and high molecular weight forms of the enzyme. The low molecular weight form does not contain these areas due to the loss of the first 158 residues after enzymatic degradation. As a result, antibodies directed against these peptides only bound the high molecular weight forms of urokinase, providing compositions for simple discriminating assays. The six peptides that were found useful in generating the A chain specific antibodies include: SNELHQVPSNCD (Seq. ID No. 1), RGKASTDTMGRPCLP (Seq. ID No. 2), CRNPDNRRRP (Seq. ID No. 3), RNPDNRRRPWC (Seq. ID No. 4), CMVHDGADGK (Seq. ID No. 5) and MVHDCADGK (Seq. ID No. 6).

Peptides derived from the carboxyl terminus of urokinase including residues 159-411 were used to generate antibodies specific for the B chain of urokinase also known as the low molecular weight (LMW) form or 33,000 dalton form of urokinase. Six peptides that found use in generating B chain specific antibodies include: YRRHRGGSVTYVC (Seq. ID No. 7), CFIDYPKKEDY (Seq. ID No. 8), SRLNSNTQGEMK (Seq. ID No. 9), SMYNDPQFGTSC (Seq. ID No. 10), LISHRECQQPHYYGSEVTTKMLC (Seq. ID No. 11), and SHTKEENGLAL (Seq. ID No. 12).

Other especially useful peptides encompass the peptide bond between lysine 158 and isoleucine 159. These peptides were used to generate antibodies that bind to the urokinase zymogen, also known as the single chain urokinase plasminogen activator (ScuPA). Two peptides that found use in generating urokinase zymogen specific antibodies include: PRFKIIG (Seq. ID No. 13) and RPRFKIIGGE (Seq. ID No. 14). Additional compositions may be considered as immunogens in the preparation of antibodies useful for this invention, for example carbohydrates linked to urokinase or other biochemical or chemical modifications to the urokinase polypeptide chain or peptide sequences homologous to urokinase sequences. Additionally, combinations of the peptides discussed above, as mixtures, and covalently attached in groups of two or more may be useful.

Immunization

Peptides may be used for immunization directly, after formulation or after conjugation to a carrier molecule. Examples of formulations for peptide immunogen injection include Freund's adjuvant. Carrier molecules that can be used to conjugate to peptide immunogens include bovine serum albumin (BSA), lysozyme, and polysaccharides such as dexetrins.

Antisera Against Peptides

Antibodies against the synthetic peptides were raised in mice by two methods (a) immunization by peptide-protein conjugates: Mice were injected and boosted with the peptide-SuBSA conjugate (50 µg per mouse) as an emulsion in complete Freund's adjuvant in the footpads and subcutaneously in the neck. Serial bleedings from 10 days prior, up to 230 days after, the first injection will be collected and studied separately. (b) Immunization with free peptide: In view of the finding (Young et al., *Immunol. Commun.*, 11:9-16 (1982)) that small synthetic peptides (6 residues or larger), when immunized in their free form in complete Freund's adjuvant, will stimulate an in vivo antibody response, peptides were injected into mice in their free form (i.e., without coupling to carrier). Each animal received peptide (25-50 µg per mouse) as an emulsion in complete Freund's adjuvant distributed into three sites as above. The animals were boosted with similar doses 3 weeks after the first injection and thereafter monthly. Serial bleedings from 10 days before, up to 200 days after, the initial injection were studied separately.

Monoclonal Antibody Preparation

Methods for preparing monoclonal antibodies are well established. See for example, *Monoclonal Antibodies*, eds. Roger H. Kennett, Thomas J. McKearn, Kathleen B. Bechtol, Plenum Press, New York, 1980; *Nature* (1975) 256:495-497.

The discovery (Young et al., (1982), id.) that synthetic peptides will evoke antibody formation when used as immunogens in their free form (i.e., without coupling to a carrier) was exploited to prepare monoclonal antibodies with preselected submolecular binding specificities to desired protein regions (Schmitz, et al., *Mol. Immunol.*, 19:1699-1702 (1982)). Peptides representing antigenic sites as well as synthetic peptides representing surface regions that are not antigenic when the whole molecule is used as an immunogen have been shown to produce antisera and subsequently monoclonal antibodies of preselected specificities (Schmitz, et al., *Mol. Immunol.*, 20:719-726 (1983); Schmitz, et al., *Mol. Immunol.*, 12:161-175 (1983)).

Mice were immunized as above with a given synthetic peptide (25-50 µg) in complete Freund's adjuvant and boosted and test-bled at 3 week intervals until high antibody titer was obtained in the test sera. Somatic cell fusions, hybridoma selection, limiting dilution cloning and subcloning, and hybrid cell expansion were performed as described by Schmitz et al. (Schmitz, et al., (1982) id.). Expanded subclones were also injected into BALB/cByJ mice ($2\times10^6$ cells/1.0 ml. fresh tissue culture media) that had been primed with pristane (Sigma Chemical Co., St. Louis, Mo.). Ascites fluid was collected, clarified and stored frozen at $-20°$ C. until screened for the presence of hybridoma antibodies.

Essentially the peptide immunogen is injected into an animal, then cells producing a useful composition are immortalized and identified. Additional injections at timed intervals may be used to increase the titer and avidity of the antibodies in the serum. Polyclonal antibodies are prepared by removing serum from these animals. Usually mice are the animal of choice and spleen cells that produce antibodies are immortalized by fusion to immortal mouse myeloma cells, for example SP/2 or 653 cells. Other animals may also be used to generate monoclonal antibodies including chickens or goats or any animal with cells that produce an antibody molecule such that the productive cell can be immortalized. Immortalization of the producing cell is needed to produce a stable starting material for the repeated production of the useful monoclonal antibodies when required. Techniques for cell immortalization include: fusion to immortal cells where the fused cell product continues to express the useful immunoglobulin, or viral infection may be used to immortalize productive cells.

Screening for antibodies with desired specificity can be performed using any of a variety of methods. In a Western blot method, protein of interest is immobilized on a solid surface, such as nitrocellulose, can be incubated with hybridoma supernatants or serum and $^{125}$I-labelled anti-mouse IgG, following removal of the incubation medium and washing of the surface, radioactivity that is bound to the surface is measured. Another method involves addition of the original peptide immunogen to the well of a growing hybridoma culture and looking for blebs or disruptions in the growing cell monolayer. Disruptions are an indication that the hybridoma is producing antibodies against the added immunogen.

Monoclonal antibodies have been prepared which are of use in the present invention. Murine monoclonal antibodies produced from clones A3-E5-A7, A3-E5-B8, A3-E5-G10, A3-E5-H12, A3-E5-B3, A3-E5-D1 were produced against the peptide immunogen PRFKIIG (Seq. ID No. 13). Murine monoclonal antibodies produced from clones C2-A4-H4, C2-A4-F10, C2-A4-F11 were produced against the peptide immunogen RPRFKIIGGE (Seq. ID No. 14). Murine monoclonal antibodies produced from clones D4-A5-E7, D4-C1-A5, D4-C1-G4, D4-C6-A4, D4-C6-A8, D4-C6-E12, D4, C6-F7 and D4-C6-G12 were directed against the peptide RPRFKIIGGE (Seq. ID No. 14) after it was chemically conjugated to bovine serum albumin.

Polyclonal Antibody Preparation

Essentially any animal that generates an immune response could be used to generate useful polyclonal antibodies for this invention. Animals commonly used include goats, sheep, rats, rabbits, chickens and cows. Particular polyclonal antibody preparations that find use in this invention were prepared from mice and rabbits. Peptides that were of use in generating antibodies against the low molecular weight form of urokinase include YRRHRGGSVTYVC (Seq. ID No. 7), CFIDYPKKEDY (Seq. ID No. 8), SRLNSNTQGEMK (Seq. ID No. 9), SMYNDPQFGTSC (Seq. ID No. 10), LISHRECQQ-PHYYGSEVTTKMLC (Seq. ID No. 11), SHTKEENGLAL (Seq. ID No. 12). These antibodies were chemically conjugated to BSA prior to injection. Chemical conjugation is not always required. For example, useful antibodies were also generated against the free peptides CFIDYPKKEDY (Seq. ID No. 8), SRLNSNTQGEMK (Seq. ID No. 9), and SMYND-PQFGTSC (Seq. ID No. 10) in mice. Other peptides that produced polyclonal antibodies of use in this invention include SNELHQVPSNCD (Seq. ID No. 1), RGKASTDT-MGRPCLP (Seq. ID No. 2), CRNPDNRRRP (Seq. ID No. 3), RNPDNRRRPWC (Seq. ID No. 4), CMVHDGADGK (Seq. ID No. 5) and MVHDCADGK (Seq. ID No. 6). Polyclonal antibodies are conveniently prepared by injecting animals with immunogen as described above.

Serum is removed from the animal and prepared by conventional techniques as described above. A blood clot is formed spontaneously. The clot is removed and the remaining serum can be purified further. The IgG molecules can be purified away from the serum by affinity chromatography to immobilized protein A or protein G. Proteins that lack an IgG heavy chain constant region will not bind to this affinity resin and will be separated from the desired polyclonal IgG antibodies. Immobilized urokinase may also be used to purify the desired antibody away from other serum proteins. Elution of the bound antibodies can be achieved by using mild denaturants such as 2 molar guanidine hydrochloride or extremes of pH such as a glycine-HCl buffered solution at pH 2.5.

The antibody preparations are then screened. Immune IgG preparations or protein A were radiolabeled with $^{125}$I (Amersham Corp., Arlington Heights, Ill.) using the chloramine-T method (Hunter et al., Nature, 194:495-496 (1962)). Unbound $^{125}$I was separated from the radiolabeled sample by gel filtration on Sephadex G-25 (Pharmacia Fine Chemicals, Piscataway, N.J.). Protein-associated $^{125}$I was assayed by precipitation with 10% (v/v) trichloracetic acid.

Polyvinylchloride protein assay plates (Costar, Cambridge, Md.) were incubated for 3 hours at 37° C. with excess (1.5 µg in 50 µg of PBS/well) test and control antigens, washed extensively with PBS, and blocked with 1% BSA in PBS (100 µl/well) for 1 hr at 37° C. to prevent non-specific binding of subsequent reagents. After washing, the plates were used for binding antibody.

Sera, culture supernatants and clarified ascites fluids were screened for anti-UK antibodies using a solid phase RIA described by Sakata and Atassi (Mol. Immunol., 18:961-967 (1981) as modified by Schmitz et al. ((1982) id.). This assay was also used to determine antibody binding specificities to peptides. Briefly, RIA plates that had been coated with the appropriate test antigens (various forms of UK or peptide conjugates) were incubated for 3 hours at 37° C. with an antibody preparation (50 µl/well) appropriately prediluted in PBS-BSA so as to maximize specific binding. The plates were subsequently washed with PBS and amplified with excess (1:1000 dilution of the stock reagent in PBS-BSA) rabbit anti-mouse IgG+IgM antisera (Litton Bionetics, Kensington, Miss.) for 2 hrs at 37° C. After washing, the plates were developed with excess ($2.0 \times 10^5$ cpm in 50 µl PBS-BSA/well) $^{125}$I-labelled protein A for 2 hrs at room temperature, washed, and then separated into individual wells that are counted in a gamma counter (Beckman Instruments, Inc., Irvine, Calif.). Results are corrected for nonspecific (0.1-2%) binding detected in control wells not coated with test antigen but blocked with BSA.

When peptide-SuBSA conjugates are the immunizing antigens then antibody responses were analyzed by peptide-lysozyme (not succinyl lysozyme) conjugates since lysozyme and SuBSA do not cross-react immunochemically. Correction for non-specific binding is derived from binding to lysozyme control. When the free peptides were the antigens then antibodies were analyzed on peptide-SuBSA conjugates and employing lysozyme and SuBSA as controls.

One of the novel aspects of these antibodies is their specificity for binding only to urokinase and not to other related proteins such as trypsin or TPA.

Other Methods of Using the Compositions

Analysis of Separated Kidney Cells

Cell separation in microgravity is one of the significant new applications of space technology to basic and clinical medical research. Separations are more effective in microgravity conditions due to the lack of sedimentation and absence of other limitations imposed by physical forces. Kidney cells have been used as a model for their separation by continuous flow electrophoresis and other methods under microgravity conditions. After the cells are separated, it is important to determine their purity, viability and physiological performance. The compositions and methods provided in this invention have been used to determine these parameters.

Cancer Diagnosis and Monitoring

This invention provides methods and compositions that are useful in the diagnosis and monitoring of tumors, which produce urokinase (such as breast, prostate and adenosarcoma). Analysis can be performed on biological fluids such as blood serum, urine, saliva and semen as a way of detecting urokinase and identifying cancer development or progress. The cells are removed from the serum by centrifugation and the soluble protein fraction assayed by a sensitive ELISA or RIA technique as previously described.

Immunohistochemical methods can be used to identify the presence of urokinase in tumor biopsy specimens. For example, the tumor tissue can be quick frozen, sections can be cut and fixed with acetone on glass slides, the sections can be treated with normal serum to reduce non-specific anti-urokinase antibody binding. The antigen can be detected by exposure to unlabeled primary antibody and a labeled second antibody. Cells from five needle biopsies may be similarly tested for uPA.

Purification of Individual Forms of Urokinase

Antibodies are relatively stable macromolecules they can be immobilized on solid supports to produce useful chromatography media. The unique specificity of an antibody makes the chromatography media extremely specific for particular molecules and facilitates the purification of these molecules from complex mixtures. A variety of methodologies can be used to immobilize antibodies on solid supports. Antibodies useful to this invention can be used in this way to provide chromatography resin that will allow the purification of each form of urokinase.

The following examples are offered as illustrations and are not meant to limit the scope of the invention.

EXAMPLES

Example I

Synthesis and Purification of Peptide Immunogens

A total of 14 peptides corresponding to different areas of the urokinase molecule have been synthesized, purified and characterized. A general discussion of the chemical synthesis of peptides, their purification and characterization can be found in the Description of Preferred Embodiments above.

| Peptides Synthesized for Antibody Development | | | |
|---|---|---|---|
| (1) 1-12 | SNELHQVPSNCD | (Seq. ID No. 1) |
| (2) 59-73 | RGKASTDTMGRPCLP | (Seq. ID No. 2) |
| (3) 102-111 | CRNPDNRRRP | (Seq. ID No. 3) |
| (4) 103-113 | RNPDNRRRPWC | (Seq. ID No. 4) |
| (5) 126-135 | CMVHDGADGK | (Seq. ID No. 5) |
| (6) 127-135 | MVHDCADGK | (Seq. ID No. 6) |
| (7) 177-189 | YRRHRGGSVTYVC | (Seq. ID No. 7) |
| (8) 205-215 | CFIDYPKKEDY | (Seq. ID No. 8) |
| (9) 222-233 | SRLNSNTQGEMK | (Seq. ID No. 9) |
| (10) 319-341 | SMYNDPQFGTSC | (Seq. ID No. 10) |
| (11) 282-293 | LISHRECQQPHYYGSEVTTKMLC | (Seq. ID No. 11) |
| (12) 401-411 | SHTKEENGLAL | (Seq. ID No. 12) |
| (13) 155-161 | PRFKIG | (Seq.ID No. 13) |
| (14) 154-163 | RPRFKIIGGE | (Seq. ID No. 14) |

Example II

Preparation of Polyclonal Antibodies

A general description of the method used to prepare polyclonal antibodies can be found in Description of the Preferred Embodiments above. Antisera obtained in this way binds very strongly to the immunizing peptides as shown by solid phase RIA.

The polyclonal antisera were labelled with $^{125}I$ as described above and their binding to the peptide-lysozyme conjugate and to the low molecular weight urokinase was determined. Results represent pools of antisera from 3 mice each and varied ±1.7% or less.

TABLE 1

Antibodies against UK Peptides of the B chain bind to both correlative peptide-lysozyme conjugates and to low molecular weight urokinase, with similar affinity.

| | $^{125}I$-Antibodies bound (Δ cpm) to | |
|---|---|---|
| Antigen | Peptide-lysozyme conjugate | Low M.W. U.K. |
| peptide 177-189 (Seq. ID No. 7) | 43,940 | 45,570 |
| peptide 205-215 (Seq. ID No. 8) | 42,490 | 44,310 |
| peptide 222-233 (Seq. ID No. 9) | 45,570 | 47,520 |
| peptide 319-330 (Seq. ID No. 10) | 49,540 | 51,090 |
| peptide 319-341 (Seq. ID No. 11) | 42,590 | 43,510 |
| peptide 401-411 (Seq. ID No. 12) | 41,060 | 42,520 |

It was similarly shown that certain of the C-terminal domain peptides demonstrated binding to all forms (LMW and HMW) of urokinase with affinities comparable to the binding exhibited by the correlative free peptide.

TABLE 2

Antisera (polyclonal) Against Peptides in the common C-terminal Domain Bind All Forms of Urokinase.
SPECIFIC BINDING (CPM)

| Antigen | Mouse No. | Binding to Free Peptide | Binding to LMW | Urokinase HMW |
|---|---|---|---|---|
| Peptide 205-215 (Seq. ID No. 8) | 1 | 50033 | 30761 | 44755 |
| | 2 | 24190 | 10563 | 17550 |
| | 3 | 40467 | 23841 | 36670 |
| Peptide 222-233 (Seq. ID No. 9) | 1 | 36101 | 17354 | 26819 |
| | 2 | 52730 | 19853 | 27951 |
| | 3 | 25601 | 10635 | 17033 |
| Peptide 319-330 (Seq. ID No. 10) | 1 | 14863 | 10923 | 11699 |
| | 2 | 24374 | 9617 | 16822 |
| | 3 | 9183 | 5168 | 6833 |

The same test were run on N-terminal domain peptides with similar results against whole urokinase.

TABLE 3

Antisera (polyclonal) Binding to Urokinase Peptides and to Urokinase.
SPECIFIC BINDING

| Antigen | Mouse No. | Binding to Free Peptide | Binding to Urokinase |
|---|---|---|---|
| Peptide 1-12 (Seq. ID No. 1) | 1 | 30740 | 8726 |
| | 2 | 36318 | 3644 |
| | 3 | 27112 | 3554 |
| Peptide 59-73 (Seq. ID No. 2) | 1 | 33478 | 3554 |
| | 2 | 19784 | 3294 |
| | 3 | 25172 | 3358 |
| Peptide 102-111 (Seq. ID No. 3) | 1 | 25992 | 10414 |
| | 2 | 21596 | 6482 |
| | 3 | 36336 | 8988 |
| Peptide 103-113 (Seq. ID No. 4) | 1 | 18876 | 7220 |
| | 2 | 10964 | 8708 |
| | 3 | 12656 | 9788 |
| Peptide 126-135 (Seq. ID No. 5) | 1 | 35798 | 3784 |
| | 2 | 15668 | 2016 |
| | 3 | 21434 | 3460 |

Example III

Preparation of Monoclonal Antibodies

A general description of the method used for the preparation of monoclonal antibodies can be found in Description of Preferred Embodiments. Monoclonal antibodies were prepared with the capacity to discriminate between the three common molecular forms of urokinase. Three groups of antibodies were developed by the use of synthetic peptides which represent the areas described above. The first group of peptides consisted of areas present both in prourokinase and high molecular weight urokinase, but absent in the low molecular weight form. These six peptides were synthesized, cleaved, purified and injected into BALB/c mice for the preparation of peptide-specific antisera. Spleen cells from these mice were fused with SP/2 myeloma cells in order to prepare monoclonal antibodies. In addition, six peptides representing areas present in all three molecular forms were made. Monoclonal antibodies raised against these peptides bound all forms of urokinase but not other serine proteases.

For the differential recognition of prourokinase from high molecular weight urokinase, specific monoclonal antibodies, binding to the area of cleavage, were developed. Two peptides were constructed which represent the area around the single peptide bond that is cleaved in the activation process (i.e., conversion of the zymogen into the active enzyme). Monoclonal antibodies specific for this area only bound to urokinase zymogen but not high molecular weight urokinase.

After injection of the peptides into outbred mice, and fusion of their spleen cells, 17 monoclonal antibodies were selected for their specificity to one of the peptides (peptide 154-163, Seq. ID No. 14). A table showing the results of this screening is shown at Table 4, below.

These monoclonals were tested for binding to the different forms of urokinase by the western blot method. The nitrocellulose paper was incubated with cell culture supernatants and $^{125}$I-labelled anti-mouse IgG. Three of the monoclonals showed specific binding to single chain urokinase. The clones involved were expanded and the monoclonal antibodies purified for further characterization and testing.

Several monoclonal antibodies were also made in mice and were then tested for specificity to ScuPA, the A-chain, B-chain the cleavage bonds at Lys-158-Ile-159, the loss of Lys-158 and the cleavage bond at Lys-135-Lys136 during activation. Additional murine monoclonal antibodies and rabbit anti-urokinase monoclonal antibodies were made and tested.

TABLE 4

Antibody Titer of Urokinase Monoclonals (cpm/min of RIA)

| Clone No. | BSA-Urokinase Peptide | BSA-Non Sense Peptide | BSA Only Blank |
|---|---|---|---|
| A3-E5-A7 | 71,813 | 803 | 901 |
| A3-E5-B8 | 47,816 | 1,321 | 876 |
| A3-E5-G10 | 58,503 | 1,454 | 1,311 |
| A3-E5-H12 | 85,240 | 1,138 | 1,158 |
| A3-E5-B3 | 59,674 | 871 | 821 |
| A3-E5-D1 | 36,729 | 934 | 877 |
| C2-A4-H4 | 7,633 | 1,855 | 928 |
| C2-A4-F10 | 40,659 | 3,053 | 1,448 |
| C2-A4-F11 | 91,196 | 6,987 | 1,726 |
| D4-A5-E7 | 4,962 | 1,393 | 1,430 |
| D4-C1-A5 | 25,631 | 1,579 | 1,355 |
| D4-C1-G4 | 90,645 | 3,410 | 1,497 |
| D4-C6-A4 | 72,303 | 1,101 | 1,045 |
| D4-C6-A8 | 43,309 | 946 | 2,171 |
| D4-C6-E12 | 82,320 | 1,405 | 1,055 |
| D4-C6-F7 | 68,513 | 1,280 | 868 |
| D4-C6-G12 | 43,013 | 1,109 | 781 |

Note:
Group A; mice were immunized with free peptide 153-162 (Seq. ID No. 15)
Group C; mice were immunized with free peptide 154-163 (Seq. ID No. 14)
Group D; mice were immunized with BSA-conjugated peptide 154-163 (Seq. ID No. 14)

Example IV

Comparison of Prior Art Test for Urokinase with that of Invention

Comparison of three assay methods for measuring urokinase in supernatants from kidney cell cultures were made in order to test the efficacy of the methods and compositions of the invention with those of the prior art. Cell cultures of HEK cells were prepared as described previously above and supernatants of the cultures were isolated. The supernatants were divided into aliquots for standardization runs, and runs using one of the three test methods.

The S-244 method used a chromatogenic substrate to measure active urokinase. The method used was that of Claeson, G. et al., "Methods for Determination of Prekalikrein in plasma, Glandular Kallikrein, and Urokinase," *Haemostasis* 7:76-87 (1978), incorporated specifically herein to the extent that it provides materials and methods not otherwise provided herein. The microclot lysis assay ("MCLA") assay measures the optical density of the clots being lysed by the urokinase to determine the half-lysis time for standard concentrations. The method used was that of Lewis et al., "A Miniaturized Fibrinolytic Assay for Plasminogen Activators," *Thrombosis Res.* 64:223-234 (1991), incorporated specifically herein to the extent that it provides materials and methods not otherwise provided herein.

The molecular-specific antibody ("MSA") assay of the invention has been previously described. It is typically run as an RIA ("MSA(RIA)") method (although it can also be an ELISA assay or other non-radioactive assay) using antibodies which are specific for the intact region of the active site (158-159) on the urokinase molecule. The RIA methods utilized were similar to those previously described above for the screening of supernatants for anti-UK antibodies using solid-phase assays (Sakata and Atassi 1981, as modified by Schmitz et al. 1982). While it is possible to label either the supernatant proteins to be tested or to label the antibodies, the inventors typically label the antibodies as previously described.

All assays were calibrated against an international reference standard for urokinase (IRP-UK; National Biologics Standards Board, London). A typical standard curve for the RIA assay (specifically, those used to standardize values observed for the Run 4 Day 12 supernatants below) is shown in FIG. 1. That standard curve plots the results from three separate standard assays as net counts per minute versus microgram concentrations of urokinase in 50 microliter volumes.

Figure 2:
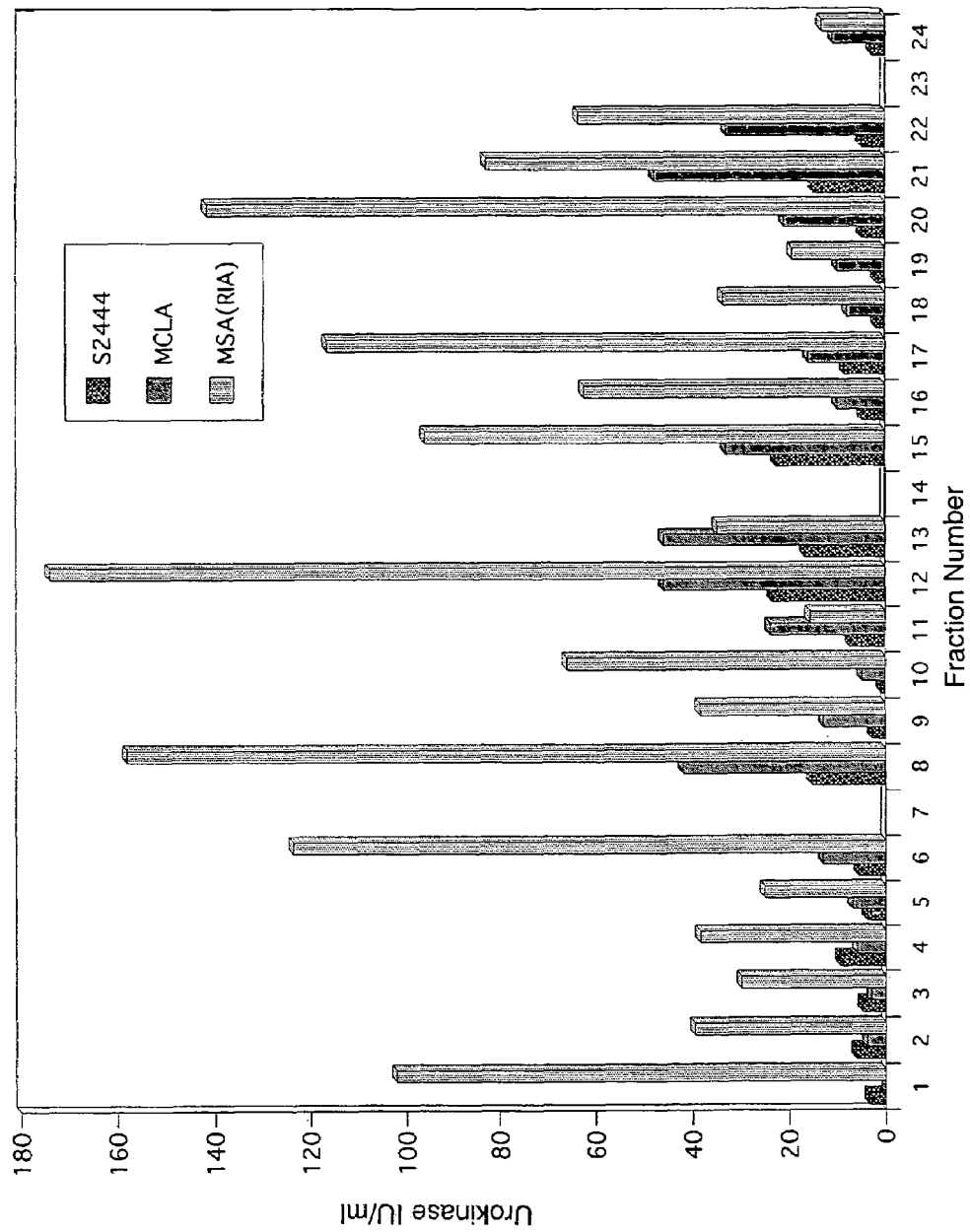
FIG. 2: Bar graph comparing amount of scuPA in the Run 4 Day 12 supernatants using two prior art methods (S-2444 and MCLA) and methods of invention (MSA-RIA).

FIG. 2 is a graph comparing the amount of scuPA in the Run 4 Day 12 supernatants using the differential S-2444 assay, the MCLA assay, and the MSA(RIA) method of the invention. The amount of scuPA contained in the supernatant culture medium harvested from four (4) day old cultures of human kidney cells, which cells had been separated by continuous flow electrophoresis into twenty-four (24) subpopulations, were determined. The estimates of scuPA found by the S-2444 assay were obtained by using two different aliquots of the supernatant and subtracting the levels of uPA activity found in the S-2444 assay (direct) and the levels found in the S-2444 assay following pre-incubation with 15 nM plasmin (2 hours at 37° C.), (which converts all of the scuPA to active two-chain uPA). This shows that the pre-incubation with plasma misses a significant amount of scuPA which is actually present in the culture medium. Conversely, the MSA is sensitive enough to measure it directly. Similarly, the MCLA assays routinely detected far less of the scuPA than did the MSA(RIA) methods of the invention.

Typically, the MCLA assay is the most comparable to the MSA(RIA) assay. Thus, for instance as can be seen in supernatant fraction 24, the two values are almost identical. Conversely, both the MCLA and the MSA(RIA) methods routinely detect substantially higher levels of scuPA than does the S-2444 assay. This was not always the case, however, since, for instance, in supernatant fractions 2-4, the S-2444 assay detected slightly more scuPA than did the MCLA assay.

However, in all instances, the MSA(RIA) assays of the invention were able to detect substantially higher levels of scuPA than the two prior art approaches.

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, the antibody preparations of the invention would be useful for whole body imaging techniques to look for tumors with elevated local concentrations of urokinase. Immunotoxins based on these antibody preparations would likewise be useful. Fragments such as Fab or Fv derived from the invention antibodies will find use in certain instances, as well. The peptides might also be used as cancer vaccines to activate the human immune system against tumors expressing urokinase. Additionally, immunoaffinity columns may be constructed with the discriminating antibodies of the invention to quantitate the different forms of urokinase in a sample (e.g., See, Sibley, et al., *Biotechniques* Vol. 10, 1993; Universal Sensors, Metairie, La.). All such modifications are intended to be included within the scope of the appended claims.

What is claimed is:

1. A method of determining total urokinase concentration in a sample containing at least one of an active or inactive form of urokinase, comprising:
    generating at least one immunological composition directed against at least one of a first peptide with SEQ ID NOs: 1, 2, 3, 4, 5 or 6;
    generating at least one immunological composition directed against at least one of a second peptide with SEQ ID NOs: 7, 8, 9, 10, 11 or 12; and
    generating at least one immunological composition directed against at least one of a third peptide with SEQ ID NOs: 13 or 14;
    contacting aliquots of said sample separately with each of said at least one immunological composition; and
    measuring quantity and comparing type of said at least one immunological composition bound in each of said aliquots to determine a concentration of said at least one of said active or inactive form of urokinase, wherein each of said at least one immunological composition binds to said at least one of said active or inactive form of urokinase and is indicative of said concentration of the form that is bound thereto, wherein the total of said concentration of said at least one of said active and inactive form of urokinase represents the total urokinase concentration in said sample.

2. The method of claim 1, wherein each of said at least one immunological composition has a binding affinity constant for said first peptide, said second peptide or said third peptide against which it is directed that is substantially higher than its binding affinity constant for a non-urokinase protein as similar in amino acid sequence to urokinase as is trypsin.

3. The method of claim 1, wherein said at least one immunological composition directed against a third peptide with SEQ ID NO: 14 exhibits a binding affinity constant for urokinase zymogen, an inactive form of urokinase, of at least $1 \times 10^8$ $M^{-1}$ and a binding affinity constant for forms of urokinase lacking a peptide bond between amino acid residues 158 and 159 of Seq ID No. 16 of at least approximately 10-fold lower than that for urokinase zymogen.

4. The method of claim 1, wherein said at least one immunological composition is an antiserum, an antibody, or a supernatent of a hybridoma.

5. The method of claim 1, wherein said determination of said quantity of each of said at least one immunological composition is carried out by radiolabeling said sample.

6. The method of claim 1, wherein said at least one active or inactive form of urokinase comprises:
    a low molecular weight urokinase that is bound to said at least one immunological composition directed against said second peptide but is not bound to said at least one immunological composition directed against said first peptide;
    a high molecular weight urokinase that is bound to said at least one immunological composition directed against said first peptide or second peptide but is not bound to said at least one immunological composition directed against said third peptide; and
    a urokinase zymogen, an inactive form of urokinase that is bound to said at least one immunological composition directed against said third peptide.

7. The method of claim 1, wherein said step of generating at least one immunological composition is further comprised of generating at least one immunological composition directed against a fourth peptide with SEQ ID NO: 17.

8. The method of claim 7, wherein said at least one of said active or the inactive form of urokinase comprises a low molecular weight urokinase that is bound to said at least one of said immunological composition directed against said second peptide, but is not bound to said immunological composition directed against said fourth peptide; and a high molecular weight urokinase in the sample that is bound to said at least one immunological composition directed against said first peptide or said second peptide, but is not bound to said immunological composition directed against said third peptide.

9. A method of determining total urokinase concentration in a sample containing at least one of an active or inactive form of urokinase, comprising:
    generating at least one immunological composition selected from a group of immunological compositions consisting of an antisera, an antibody and a supernatant of a hybridoma, each of said at least one immunological composition obtained via injection of at least one of a first peptide with SEQ ID NOs: 1, 2, 3, 4, 5 or 6;
    generating at least one immunological composition selected from a group of immunological compositions consisting of an antisera, an antibody and a supernatant of a hybridoma, each of said at least one immunological composition obtained via injection of at least one of a second peptide with SEQ ID NOs: 7, 8, 9, 10, 11 or 12; and
    generating at least one immunological composition selected from a group of immunological compositions consisting of an antisera, an antibody and a supernatant of a hybridoma, each of said at least one immunological composition obtained via injection of at least one of a third peptide with SEQ ID NOs: 13 or 14;

contacting aliquots of said sample separately with each of said at least one immunological composition;

measuring quantity and comparing type of each of said at least one immunological composition bound in each of said aliquot to determine a total concentration of said at least one of said active and inactive form of urokinase in said sample, wherein each of said at least one immunological composition binds to said at least one of said active or inactive forms of urokinase and is indicative of said total concentration of the form of urokinase that is bound thereto, said determination comprising:

determining a first concentration of low molecular weight urokinase in said sample, wherein said low molecular weight urokinase is bound to said at least one immunological composition directed against said second peptide, but is not bound to said at least one immunological composition directed against said first peptide;

determining a second concentration of high molecular weight urokinase in said sample, wherein said high molecular weight urokinase is bound to said at least one immunological composition directed against said first peptide or second peptide, but is not bound to said at least one immunological composition directed against said third peptide, and determining a third concentration of urokinase zymogen, an inactive form of urokinase, in said sample, wherein said urokinase zymogen is bound to said at least one immunological composition directed against said third peptide; and adding the first, second and third concentrations to obtain said total concentration, wherein said total concentration represents a total urokinase concentration in said sample.

10. A kit for determining total urokinase concentration in a sample containing at least one of an active or inactive form of urokinase, comprising:

immunological composition(s) directed against at least one of a first peptide with SEQ ID NOs: 1, 2, 3, 4, 5, or 6;

immunological composition(s) directed against at least one of a second peptide with SEQ ID NOs: 7, 8, 9, 10, 11 or 12;

immunological composition(s) directed against at least one of a third peptide with SEQ ID NOs: 13 or 14; and instructions for determining said total urokinase concentration in said sample by adding concentrations of said at least one of said active and inactive forms of urokinase obtained by measuring quantity and type of immunological composition(s) bound in aliquots of said sample.

11. The kit of claim 10, wherein said immunological composition(s) is further comprised of:

an immunological composition directed against a fourth peptide with SEQ ID NO: 17.

12. The kit of claim 10, wherein said immunological composition(s) is an antiserum, an antibody or a supernatant of a hybridoma.

* * * * *

SEQUENCE LISTING

```
<160> NUMBER OF SEQ ID NOS: 17

<210> SEQ ID NO 1
<211> LENGTH: 15
<212> TYPE: PRT
<213> ORGANISM: Artificial
<220> FEATURE:
<223> OTHER INFORMATION: Synthetic Peptide

<400> SEQUENCE: 1

Arg Gly Lys Ala Ser Thr Asp Thr Met Gly Arg Pro Cys Leu Pro
1               5                   10                  15

<210> SEQ ID NO 2
<211> LENGTH: 15
<212> TYPE: PRT
<213> ORGANISM: Artificial
<220> FEATURE:
<223> OTHER INFORMATION: Synthetic Peptide

<400> SEQUENCE: 2

Arg Gly Lys Ala Ser Thr Asp Thr Met Gly Arg Pro Cys Leu Pro
1               5                   10                  15

<210> SEQ ID NO 3
<211> LENGTH: 10
<212> TYPE: PRT
<213> ORGANISM: Artificial
<220> FEATURE:
<223> OTHER INFORMATION: Synthetic Peptide

<400> SEQUENCE: 3

Cys Arg Asn Pro Asp Asn Arg Arg Arg Pro
1               5                   10

<210> SEQ ID NO 4
<211> LENGTH: 11
<212> TYPE: PRT
```

```
<213> ORGANISM: Artificial
<220> FEATURE:
<223> OTHER INFORMATION: Synthetic Peptide

<400> SEQUENCE: 4

Arg Asn Pro Asp Asn Arg Arg Pro Trp Cys
1               5                   10

<210> SEQ ID NO 5
<211> LENGTH: 10
<212> TYPE: PRT
<213> ORGANISM: Artificial
<220> FEATURE:
<223> OTHER INFORMATION: Synthetic Peptide

<400> SEQUENCE: 5

Cys Met Val His Asp Gly Ala Asp Gly Lys
1               5                   10

<210> SEQ ID NO 6
<211> LENGTH: 9
<212> TYPE: PRT
<213> ORGANISM: Artificial
<220> FEATURE:
<223> OTHER INFORMATION: Synthetic Peptide

<400> SEQUENCE: 6

Met Val His Asp Cys Ala Asp Gly Lys
1               5

<210> SEQ ID NO 7
<211> LENGTH: 13
<212> TYPE: PRT
<213> ORGANISM: Artificial
<220> FEATURE:
<223> OTHER INFORMATION: Synthetic Peptide

<400> SEQUENCE: 7

Tyr Arg Arg His Arg Gly Gly Ser Val Thr Tyr Val Cys
1               5                   10

<210> SEQ ID NO 8
<211> LENGTH: 11
<212> TYPE: PRT
<213> ORGANISM: Artificial
<220> FEATURE:
<223> OTHER INFORMATION: Synthetic Peptide

<400> SEQUENCE: 8

Cys Phe Ile Asp Tyr Pro Lys Lys Glu Asp Tyr
1               5                   10

<210> SEQ ID NO 9
<211> LENGTH: 12
<212> TYPE: PRT
<213> ORGANISM: Artificial
<220> FEATURE:
<223> OTHER INFORMATION: Synthetic Peptide

<400> SEQUENCE: 9

Ser Arg Leu Asn Ser Asn Thr Gln Gly Glu Met Lys
1               5                   10

<210> SEQ ID NO 10
<211> LENGTH: 12
<212> TYPE: PRT
<213> ORGANISM: Artificial
```

```
<220> FEATURE:
<223> OTHER INFORMATION: Synthetic Peptide

<400> SEQUENCE: 10

Ser Met Tyr Asn Asp Pro Gln Phe Gly Thr Ser Cys
1               5                   10

<210> SEQ ID NO 11
<211> LENGTH: 24
<212> TYPE: PRT
<213> ORGANISM: Artificial
<220> FEATURE:
<223> OTHER INFORMATION: Synthetic Peptide

<400> SEQUENCE: 11

Leu Ile Ser His Arg Glu Cys Gln Gln Pro His Tyr Tyr Gly Ser Glu
1               5                   10                  15

Val Thr Thr Thr Lys Met Leu Cys
            20

<210> SEQ ID NO 12
<211> LENGTH: 11
<212> TYPE: PRT
<213> ORGANISM: Artificial
<220> FEATURE:
<223> OTHER INFORMATION: Synthetic Peptide

<400> SEQUENCE: 12

Ser His Thr Lys Glu Glu Asn Gly Leu Ala Leu
1               5                   10

<210> SEQ ID NO 13
<211> LENGTH: 7
<212> TYPE: PRT
<213> ORGANISM: Artificial
<220> FEATURE:
<223> OTHER INFORMATION: Synthetic Peptide

<400> SEQUENCE: 13

Pro Arg Phe Lys Ile Ile Gly
1               5

<210> SEQ ID NO 14
<211> LENGTH: 10
<212> TYPE: PRT
<213> ORGANISM: Artificial
<220> FEATURE:
<223> OTHER INFORMATION: Synthetic Peptide

<400> SEQUENCE: 14

Arg Pro Arg Phe Lys Ile Ile Gly Gly Glu
1               5                   10

<210> SEQ ID NO 15
<211> LENGTH: 10
<212> TYPE: PRT
<213> ORGANISM: Artificial
<220> FEATURE:
<223> OTHER INFORMATION: Synthetic Peptide

<400> SEQUENCE: 15

Leu Arg Pro Arg Phe Lys Ile Ile Gly Gly
1               5                   10

<210> SEQ ID NO 16
<211> LENGTH: 411
```

<212> TYPE: PRT
<213> ORGANISM: Artificial
<220> FEATURE:
<223> OTHER INFORMATION: Synthetic Peptide

<400> SEQUENCE: 16

```
Ser Asn Glu Leu His Gln Val Pro Ser Asn Cys Asp Cys Leu Asn Gly
1               5                   10                  15

Gly Thr Cys Val Ser Asn Lys Tyr Phe Ser Asn Ile His Trp Cys Asn
            20                  25                  30

Cys Pro Lys Lys Phe Gly Gly Gln His Cys Glu Ile Asp Lys Ser Lys
            35                  40                  45

Thr Cys Tyr Glu Gly Asn Gly His Phe Tyr Arg Gly Lys Ala Ser Thr
        50                  55                  60

Asp Thr Met Gly Arg Pro Cys Leu Pro Trp Asn Ser Ala Thr Val Leu
65                  70                  75                  80

Gln Gln Thr Tyr His Ala His Arg Ser Asp Ala Leu Gln Leu Gly Leu
                85                  90                  95

Gly Lys His Asn Tyr Cys Arg Asn Pro Asp Asn Arg Arg Arg Pro Trp
            100                 105                 110

Cys Tyr Val Gln Val Gly Leu Lys Pro Leu Val Gln Glu Cys Met Val
            115                 120                 125

His Asp Cys Ala Asp Gly Lys Lys Pro Ser Ser Pro Glu Glu Leu
            130                 135                 140

Lys Phe Gln Cys Gly Gln Lys Thr Leu Arg Pro Arg Phe Lys Ile Ile
145                 150                 155                 160

Gly Gly Glu Phe Thr Thr Ile Glu Asn Gln Pro Trp Phe Ala Ala Ile
                165                 170                 175

Tyr Arg Arg His Arg Gly Gly Ser Val Thr Tyr Val Cys Gly Gly Ser
            180                 185                 190

Leu Ile Ser Pro Cys Trp Val Ile Ser Ala Thr His Cys Phe Ile Asp
            195                 200                 205

Tyr Pro Lys Lys Glu Asp Tyr Ile Val Tyr Leu Gly Arg Ser Arg Leu
210                 215                 220

Asn Ser Asn Thr Gln Gly Glu Met Lys Phe Glu Val Glu Asn Leu Ile
225                 230                 235                 240

Leu His Lys Asp Tyr Ser Ala Asp Thr Leu Ala His His Asn Asp Ile
                245                 250                 255

Ala Leu Leu Lys Ile Arg Ser Lys Glu Gly Arg Cys Ala Gln Pro Ser
            260                 265                 270

Arg Thr Ile Gln Thr Ile Cys Leu Pro Ser Met Tyr Asn Asp Pro Gln
            275                 280                 285

Phe Gly Thr Ser Cys Glu Ile Thr Gly Phe Gly Lys Glu Asn Ser Thr
        290                 295                 300

Asp Tyr Leu Tyr Pro Glu Gln Leu Lys Met Thr Val Val Lys Leu Ile
305                 310                 315                 320

Ser His Arg Glu Cys Gln Gln Pro His Tyr Tyr Gly Ser Glu Val Thr
                325                 330                 335

Thr Lys Met Leu Cys Ala Ala Asp Pro Gln Trp Lys Thr Asp Ser Cys
            340                 345                 350

Gln Gly Asp Ser Gly Gly Pro Leu Val Cys Ser Leu Gln Gly Arg Met
            355                 360                 365

Thr Leu Thr Gly Ile Val Ser Trp Gly Arg Gly Cys Ala Leu Lys Asp
        370                 375                 380
```

-continued

```
Lys Pro Gly Val Tyr Thr Arg Val Ser His Phe Leu Pro Trp Ile Arg
385                 390                 395                 400

Ser His Thr Lys Glu Glu Asn Gly Leu Ala Leu
                405                 410

<210> SEQ ID NO 17
<211> LENGTH: 9
<212> TYPE: PRT
<213> ORGANISM: Artificial
<220> FEATURE:
<223> OTHER INFORMATION: Synthetic Peptide

<400> SEQUENCE: 17

Ala Asp Asp Gly Lys Lys Pro Ser Ser
1               5
```